(12) United States Patent
Nguyen-DeMary et al.

(10) Patent No.: US 8,684,982 B2
(45) Date of Patent: Apr. 1, 2014

(54) CONTROLLED EVACUATION OSTOMY APPLIANCE

(75) Inventors: Tinh Nguyen-DeMary, Milltown, NJ (US); Mingliang Lawrence Tsai, Holmdel, NJ (US)

(73) Assignee: Convatec Technologies Inc., Las Vegas, NV (US)

( * ) Notice: Subject to any disclaimer, the term of this patent is extended or adjusted under 35 U.S.C. 154(b) by 0 days.

(21) Appl. No.: 13/282,015

(22) Filed: Oct. 26, 2011

(65) Prior Publication Data

US 2012/0283678 A1 Nov. 8, 2012

Related U.S. Application Data

(60) Provisional application No. 61/407,943, filed on Oct. 29, 2010.

(51) Int. Cl.
*A61F 5/448* (2006.01)

(52) U.S. Cl.
USPC ............ 604/337; 604/317; 604/327; 604/332

(58) Field of Classification Search
USPC ......... 604/319, 321, 324, 332, 336, 337, 338, 604/339, 341, 342, 344, 348, 367, 369, 604/385.01
See application file for complete search history.

(56) References Cited

U.S. PATENT DOCUMENTS

| 4,411,659 | A | * | 10/1983 | Jensen et al. | 604/332 |
| 4,889,534 | A | * | 12/1989 | Mohiuddin et al. | 604/339 |
| 6,312,415 | B1 | * | 11/2001 | Nielsen et al. | 604/342 |
| 6,572,588 | B1 | * | 6/2003 | Bierman et al. | 604/180 |
| 2004/0181197 | A1 | * | 9/2004 | Cline | 604/337 |
| 2004/0267198 | A1 | * | 12/2004 | Torstensen et al. | 604/104 |
| 2006/0058576 | A1 | * | 3/2006 | Davies et al. | 600/32 |

FOREIGN PATENT DOCUMENTS

| WO | WO2008/141180 | * 11/2008 | ............... A61F 5/44 |
| WO | WO-A-2008/141180 | 11/2008 | |

* cited by examiner

*Primary Examiner* — Jackie Ho
*Assistant Examiner* — Eric Bryant
(74) *Attorney, Agent, or Firm* — Wilson, Sonsini, Goodrich & Rosati

(57) ABSTRACT

A controlled evacuation ostomy appliance comprises a pouch having a non-entrant stoma seal and a retainer for retaining the lower portion of the pouch in the folded-up condition. The appliance optionally includes a body fitment that may include a region of manually moldable adhesive for forming a custom fit at the stoma.

32 Claims, 10 Drawing Sheets

CONTROLLED EVACUATION OSTOMY APPLIANCE

FIELD OF THE INVENTION

The present invention relates to an ostomy appliance for managing effluent from a stoma. Some aspects of the invention relate to a controlled discharge ostomy appliance. Some aspects of the invention relate to appliance with an external stoma seal. Some aspects of the invention relate to an appliance with an integral waste collector. Some aspects of the invention relate to a prosthetic ostomy appliance.

BACKGROUND TO THE INVENTION

WO-A-2008/141180 (the content of which is incorporated herein by reference in its entirety) describes a controlled discharge ostomy appliance comprising a pouch having first and second walls, with an inlet aperture in the first wall. A stoma seal is carried by the second wall, and is disposed generally in register with the inlet aperture for sealing against a stoma in use. An outer coupling element is coupled to the first wall and surrounds the inlet aperture. An inner coupling element for supporting the stoma seal, is coupled to the second wall and/or to the stoma seal. The outer coupling member surrounds a periphery of the inner coupling element. The stoma seal may be of an inflatable type, or a foam based type, or a film based type, or an insertable type. Manipulation tabs may be provided associated with the inner and outer coupling elements. The pouch includes a rectangular tail that is distensible from a compact folded-up configuration to a distended configuration when a discharge of effluent into the pouch is desired.

One feature of the above design is the presence of inner and outer coupling elements, that provide control of the position of the seal with respect to the inlet aperture. Although an external seal is contemplated, other illustrated embodiments include a seal that is insertable into the stoma and is, for example, inflated to achieve the desired sealing function.

SUMMARY OF THE INVENTION

The present invention appreciates that further improvements to the above design of ostomy appliance may enhance yet further the advantages and usefulness of the appliance for an ostomate.

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

Broadly speaking, one aspect of the invention provides a controlled evacuation ostomy appliance comprising a stomal aperture, a non-entrant stoma seal, an inner coupling member coupled to support the stoma seal for retaining the stoma seal in an operative position with respect to the stoma aperture, and outer coupling member around the inner adhesive member for supporting the appliance on the body.

Some embodiments are directed to enhancing control over the seal applied to the external tissue of the stoma. There are conflicting requirements for the seal that complicate the design. Especially in the case of a non-entrant seal, the seal pressure should be sufficiently great to achieve a reliable seal merely from the outside of the stoma. However, prolonged application of significant sealing pressure should preferably be avoided, in order to avoid any perceived risk of reduced blood perfusion in the stoma tissue.

In some embodiments of the invention, the stoma seal is positioned relative to the stomal aperture such that, in use and with a stoma in a quiescent or rest state, the stoma seal just touches the stoma and/or exerts a seal pressure on the stoma of not more than about 1 psi (51.7 mm Hg). When the stoma becomes active, the force of stool within the intestine urges the stoma outwardly against the stoma seal. The stoma seal resists by applying a reaction pressure against the outwardly urged stoma. The stoma seal is supported in position by the inner coupling member. The stoma seal exerts a seal pressure on the stoma not more than about 2 psi (103.4 mm Hg) when the stoma becomes active. Such an arrangement takes advantage of the fact that when the stoma is at rest, little or no seal effect is needed against the stoma. The stoma seal has little contact and/or seal pressure against the stoma, avoiding any concerns of prolonged application of significant sealing pressure applied to the stoma tissue. Yet the stoma seal is supported by the inner coupling member, and is able to withstand outward challenges from the stoma by applying a reactive sealing pressure.

Additionally or alternatively, in some embodiments of the invention, the stoma seal comprises a polymeric foam having a Shore A hardness of less than about 80, and optionally less than about 40. The plastics foam may directly contact the stoma (especially over the Shore A hardness range of up to about 40), or an additional seal membrane or panel may provide the seal contact surface (especially over the Shore A hardness range of up to about 80). The foam may be open cell or closed cell (or a mix of both).

Additionally or alternatively, in some embodiments of the invention, the stoma seal is resiliently deformable, and is configured to generate a reaction pressure of not more than about 2 psi (preferably not more than about 1 psi, preferably not more than about 0.8 psi) when the stoma seal is compressed or deflected. The amount of stoma seal compression could be at least 5%, or preferably, at least 10%. Such a relatively soft stoma seal can provide excellent conformity to closely follow the contour of the stoma, without risk of exerting excessive force.

Additionally or alternatively, in some embodiments of the invention, the inner coupling member is configured to transmit to a counterpart member or surface to which the inner coupling member couples, a reaction force borne by the stoma seal. The inner coupling member is configured to release or separate from a coupled condition with the counterpart member or surface when the stoma seal reaction force exceeds a seal threshold. The seal threshold may, for example, be not greater than 1 psi (51.7 mm Hg), or preferably not greater than 0.8 psi (41 mm Hg). The use of such selective coupling strength for the inner coupling member can ensure that the seal force applied to the stoma by the stoma seal does not exceed a safe level. In the event of the reaction to the seal force exceeding the seal threshold, the inner coupling member will begin to separate or release, thereby to relieve the seal force. The seal threshold of outer coupling member may be at least 10 N/in shear strength (i.e., 0 degree peel) or 5 psi such that the device will remain attached to the peristomal skin even though the inner coupling member is separated or released its contact against the stoma.

The coupling members may be of any suitable type, for example, adhesive, mechanical interference fit, or magnetic, or a combination of two or more of these. The coupling members may be of the same type or different types. The counterpart member/surface may optionally be the same member/surface for both the inner and outer coupling members. For example, in the case of adhesive coupling members, a counterpart surface could be a wearer's skin, or a plastics landing surface of a separate body fitment attachable to the body.

In some embodiments, the inner and outer coupling members couple to a body fitment providing the interface to the wearer's body. The body fitment may be separate from the appliance, or it may be captive to the appliance before engagement of the coupling members with the body fitment. For example, the body fitment may be integrally coupled to the appliance by a flexible or pivoting link. Additionally or alternatively, the body fitment may include a region of skin adhesive that is manually moldable or shapeable to define a custom shaped fit around an individual's stoma. Additionally or alternatively, the first coupling member may be for a substantially non-separable coupling with the body fitment once coupled together, such that the body fitment is not removable thereafter.

Broadly speaking, a further aspect of the invention provides a controlled evacuation ostomy appliance comprising a pouch having first and second walls. The first wall includes a first aperture for receiving a stoma. The appliance further comprises a seal for selectively blocking discharge from the stoma into the pouch. The pouch comprises an upper portion in which the first aperture is located, and a lower portion. The lower portion is deployable, either automatically or manually, from a folded-up configuration to a distended configuration.

In some embodiments, the lower portion is wider in the plane of the pouch than (i) the upper portion and/or (ii) a necked portion between the upper and lower portions. In the folded-up configuration, at least one side region of the lower portion is folded inwardly to define a lower portion of reduced width in the plane of the pouch, and the lower portion with the inwardly folded side(s) is subsequently folded towards the upper portion.

When deployed to the distended configuration, lower portion is distended downwardly away from the upper portion, and the at least one side region of the lower portion unfolds to provide the full width.

Such an arrangement can provide increased collection volume for the lower portion of the pouch and/or reduce the length of distension to achieve a desired collection volume. The reduced width of the lower portion (with the side region(s) folded inwardly) may optionally have substantially the same width as the upper region or necked region, as appropriate. The reference to "substantially the same width" means to within about 2 cm and/or 20% of the width.

Additionally or alternatively, in some embodiments, the appliance further comprises a flexible cover that substantially covers the second wall in the upper region of the pouch. The flexible cover includes an integral retainer for retaining the lower portion of the pouch in the folded-up configuration. The flexible cover may optionally be made from a rubber or thermoplastic elastomer to provide a soft, comfortable and impact absorbing surface.

The retainer may be manually releasable or displaceable to allow the folded-up lower portion of the pouch to deploy to its distended configuration. The retainer may, purely by way of example, be in the form of a clip, pocket, channel, or fastener.

The flexible cover may cover all of the second face of the upper portion of the pouch such that no part of the second face of the upper portion is visible.

A further aspect of the invention provides a controlled evacuation ostomy appliance comprising one or more of: a pouch having first and second walls, the first wall including a stomal aperture; a non-entrant stoma seal; an inner coupling member coupled to support the stoma seal for retaining the stoma seal in an operative position with respect to the stomal aperture; an outer coupling member around the inner coupling member for supporting the appliance; a cover of flexible impact-absorbing material covering at least a portion of the second wall opposite the stomal aperture, the cover comprising a retainer for retaining the lower portion of the pouch in the folded-up condition. The appliance optionally includes a body fitment that is permanently attachable and/or captive to at least the outer coupling member. The body fitment may include a region of manually moldable adhesive for forming a custom fit at the stoma.

Other aspects of the invention are defined in the appended claims. Protection may also be claimed for any novel feature or idea described herein and/or shown in the drawings whether or not emphasis has been placed thereon.

DETAILED DESCRIPTION OF PREFERRED EMBODIMENTS

Figure 1:
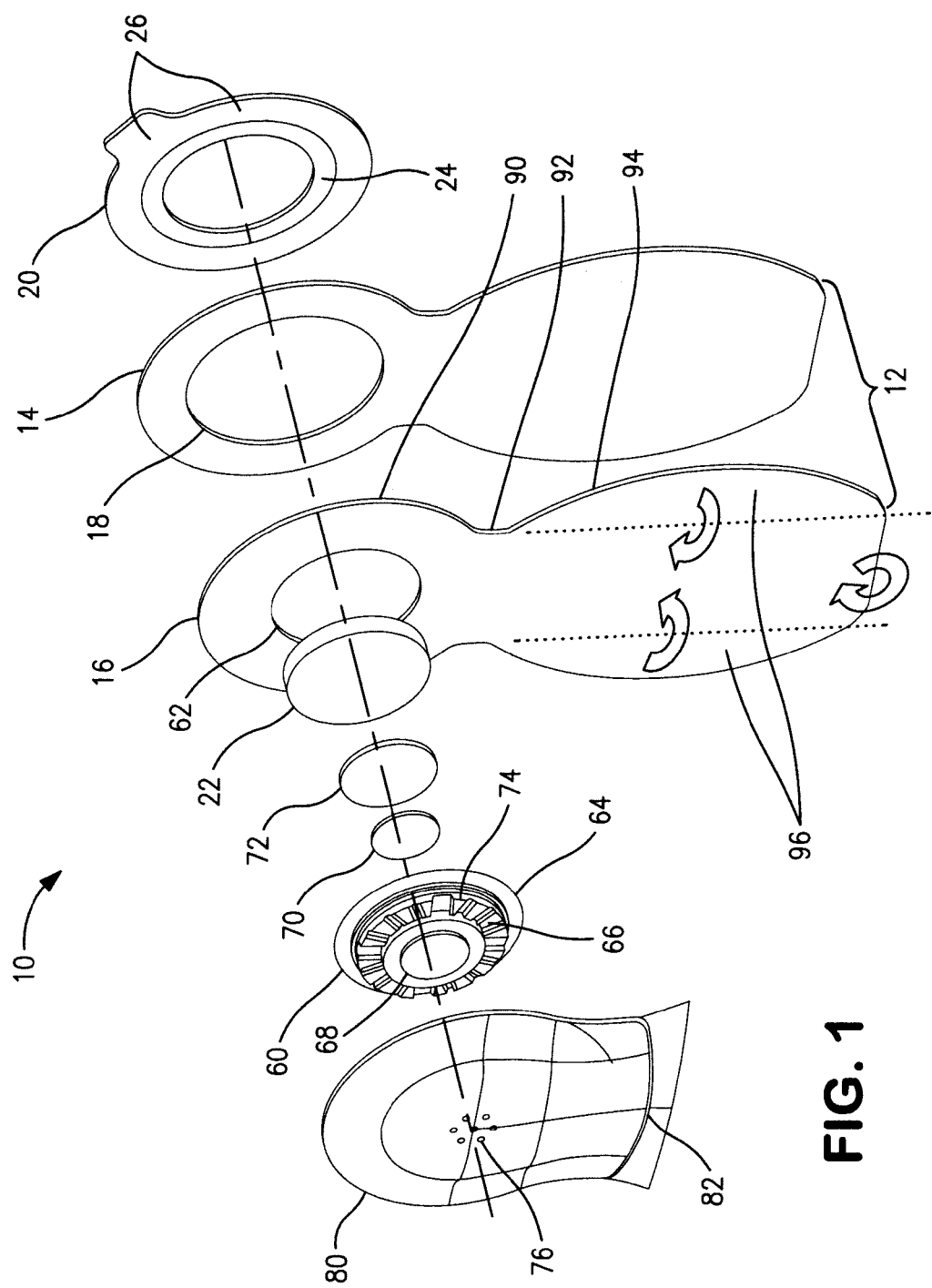
FIG. 1 is a schematic exploded view through a first embodiment of controlled discharge ostomy appliance in accordance with the invention.

In the following description, the same reference numerals are used in different embodiments to denote equivalent or similar features.

Referring to the drawings, embodiments of a controlled discharge ostomy appliance 10 are illustrated. The appliance 10 generally comprises a pouch 12 having a first (rear) wall 14 and a second (front) wall 16. The first wall 14 comprises a first aperture 18. A first (outer) annular coupling member 20 is attached to the first wall 14 at the first aperture 18. The first coupling member 18 supports the weight of the appliance in use, when worn on the body. The term annular may mean any shape having a closed loop form around an aperture, whether round or other shape, and whether or not the coupling member resembles a ring. At least a portion of the first coupling member 20 may circumscribe the first aperture 18.

Figure 3:
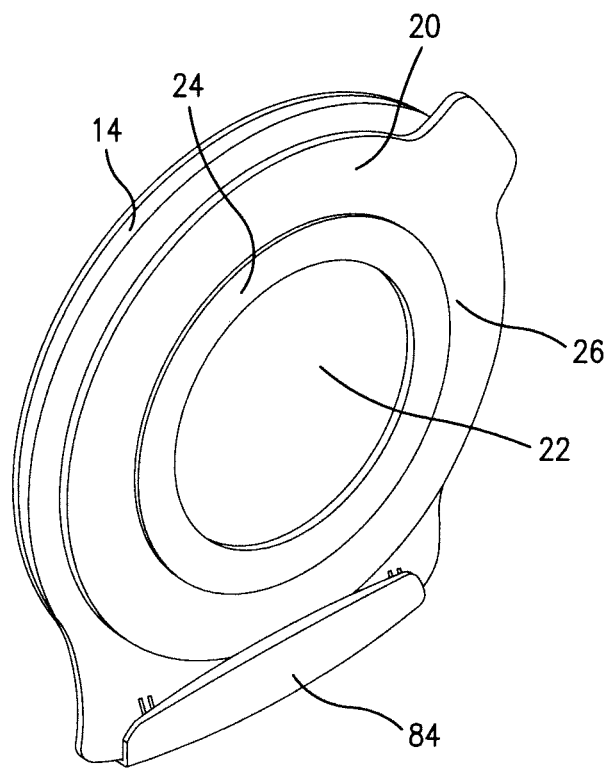
FIG. 3 is a schematic rear perspective view of the first embodiment with the pouch in a stowed condition.

The appliance further comprises a stoma seal 22. The stoma seal 22 is a non-entrant seal that occludes a stoma 28 (FIG. 5), in use, by contact with an external surface of the stoma 28 without substantially entering the stoma 28. The stoma seal 22 is carried within the pouch 12 by the second wall 16. The stoma seal 22 is additionally supported at an operative sealing position (FIGS. 3, 5 and 7) at the first aperture 18, by means of a second coupling member 24. The second coupling member 24 is disposed, or nests, radially within the first coupling member 20. The first and second coupling members 20 and 24 may optionally be coaxial, and further optionally concentric. The first and second coupling members 20 and 24 may be separate items, or they may initially be integral with each other and coupled by one or more frangible bridges or connections 26. The first and second coupling members 20 and 24 are configured to couple to one or more counterpart coupling surfaces or elements (indicated in phantom). The second coupling member 24 is separable from its counterpart surface or element without separating the first coupling member 20, to allow the stoma seal 22 to be displaced to a non-sealing position (FIG. 6), leaving the appliance attached via the first coupling member 20. In the non-sealing position, the stoma seal 22 remains carried by the second wall 16, as mentioned above. Such an arrangement enables the seal 22 to be manipulated through the second wall 16 without having to remove or open the pouch 12 to access the stoma seal 22 directly.

Figure 5:
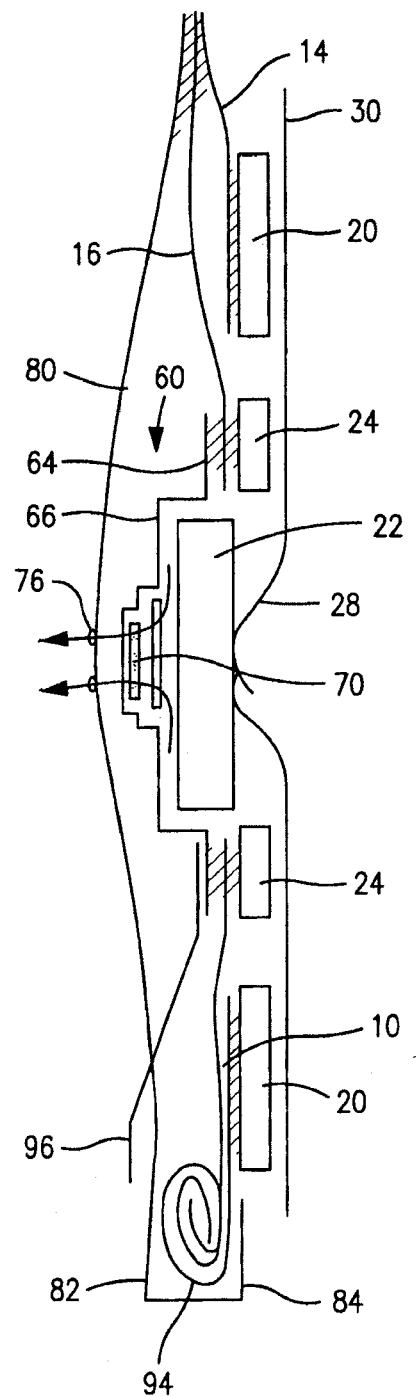
FIG. 5 is a schematic section through the first embodiment shown worn directly on the body in an operative sealing position.
Figure 7:
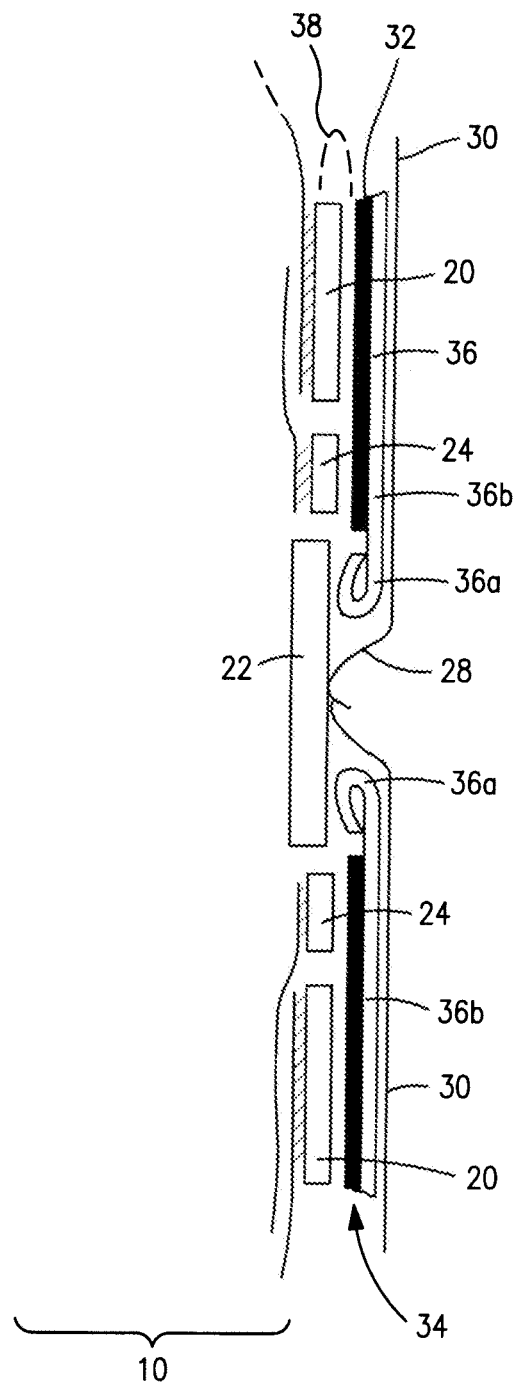
FIG. 7 is a schematic section through a part of the first embodiment in a version employing a body fitment.

The first and second coupling members 20 and 24 may be selected from adhesive, mechanical (e.g. interference or interlock fit) or magnetic. The first and second coupling members 20 and 24 may be of the same type, e.g. both adhesive, or they may be of different types. If adhesive, the coupling members 20 and 24 may comprise skin-compatible adhesive for direct attachment to skin 30 as the counterpart surface for mounting the appliance at the stoma 28 (FIG. 5). Alternatively (FIG. 7), all types of coupling member may be configured for attachment to a counterpart element 32 that is part of a body fitment 34 to which the coupling members 20 and 24 are configured to attach. The body fitment 34 comprises, for example, a layer or pad of skin-compatible adhesive 36 facing towards the body, and the counterpart surface or element 32 facing towards the appliance 10. FIG. 7 illustrates a single or common counterpart element 32 for both coupling members 20 and 24, although the body fitment 34 could, if desired, comprise respective different or distinct counterpart coupling elements/surfaces for the first and second coupling members 20 and 24. In the case of adhesive attachment, the coupling member 20 or 24 may comprise adhesive, and the counterpart element 32 may comprise a non-adhesive landing surface; alternatively the adhesive may be provided on the counterpart element 32 and the coupling member 20 or 24 may comprise a non-adhesive landing surface; alternatively both the coupling member 20 or 24 and the counterpart element may be adhesive.

In FIG. 7, the body fitment 34 may be of a type that is separate or separable from the appliance 10. Such a body fitment 34 may remain worn on the skin 30 allowing the appliance 10 to be removed and interchanged with a replacement appliance without removing the body fitment 34 from the skin. Such an arrangement may be referred to as "two-piece".

Alternatively, in FIG. 7, the body fitment 34 may be intended to form a non-separable attachment to the first coupling member 20 at least after the first time that the body fitment is assembled to engage with the first coupling member 20. Such an arrangement may be referred to as "assemblable one-piece". As used herein, the term non-separable may mean a connection sufficiently strong that the appliance 10 cannot easily be separated from the body fitment 34 (i) at least while worn on the body and/or (ii) without risk of damage to one or both components. For example, the first coupling member 20 may comprise an adhesive forming a bond that is stronger than the adhesive attachment between the adhesive pad 36 and the wearer's skin 30. The bond for the first coupling member 20 may be substantially permanent. Instead of strong adhesive, the non-separable attachment may be mechanical, for example, formed by a strong non-separable interlock, e.g. stronger than the adhesive bond to the body. In contrast to the first coupling member 20, the second coupling member 24 is (as mentioned above) configured to be separable from the body fitment 34 in order to allow the seal 22 to be moved to a non-sealing position.

In the assemblable one-piece example, the body fitment 34 may be wholly separate from the appliance prior to assembling the body fitment 34 to the appliance 10. Alternatively, the body fitment 34 may be captive to the appliance 10, for example attached by a flexible or articulating link or joint 38. In one example, the body fitment 34 and the first and second coupling members 20 and 24 may comprise portions of an integral web that flexes at a region between the body fitment 34 and the first and second coupling members 20 and 24. The web may define or include the aforementioned frangible connections between the first and second coupling members 20 and 24.

In the example body fitment 34 of FIG. 7, the adhesive pad 36 optionally includes a moldable zone 36a around the stoma 28, and a non-moldable zone 36b circumscribing the moldable zone 36a. The moldable zone 36a permits a user to manually shape an aperture in the adhesive to form a custom fit to the unique shape of the individual ostomate's stoma 28. In the preferred form, the moldable and non-moldable zones 36a and 36b are integral portions of the same pad 36. The moldable zone 36a may be manually shaped by rolling or folding back the inner rim of adhesive towards the face of the adhesive pad 36a facing away from the body. Within the moldable zone 36a, the face of adhesive facing towards away from the body may comprise exposed adhesive to facilitate adhesive anchoring of the rim in its rolled or folded back condition, and thereby hold the moldable zone 36a in its molded shape. The provision of the moldable zone 36a on a body fitment that is (at least initially) distinct from and/or uncoupled with respect to the coupling members 20 and 24 of the appliance 10 facilitates access to and molding of the adhesive pad 36 from the non-body-facing side (i.e. the side normally facing the first and second coupling members 20 and 24). Depending on the design, it may also facilitate fitting and seating of the body fitment 34 on the body around the stoma 28 before the first and second coupling members 20 and 24 are engaged with the body fitment 34. The body fitment 34 with a moldable zone 36a may be used either as a body fitment that is separate and/or separable from the appliance, or captive to the appliance.

Various constructions of stoma seal 22 are envisaged. Generally, the stoma seal 22 is of an external or non-entrant type that seals against the external tissue of the stoma, without penetrating or entering substantially the stoma lumen.

Figure 8:
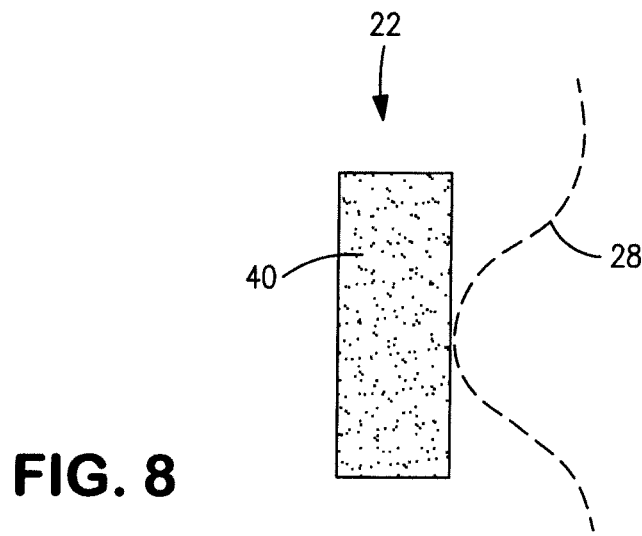
FIG. 8 is a schematic section showing in isolation a first example of stoma seal.
Figure 9:
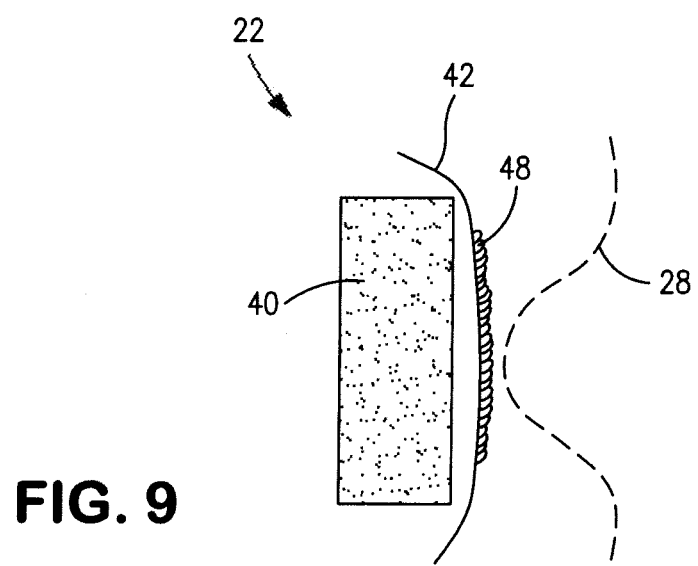
FIG. 9 is a schematic section showing in isolation a second example of stoma seal.
Figure 10:
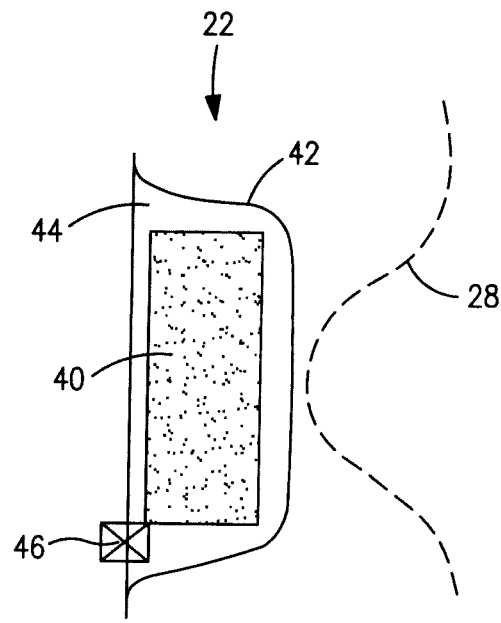
FIG. 10 is a schematic section showing in isolation a third example of stoma seal.

Referring to FIGS. 8-10, a first example of stoma seal 22 comprises a resilient member 40. The resilient member 40 may directly contact the stoma 28 in use (FIG. 8), or the resilient member 40 may optionally be covered by a seal membrane 42 (FIG. 9) that faces and contacts the stoma 28 in use. The seal membrane 42 may be of material that is substantially impervious to liquid and gas, in order to prevent effluent and flatus from contacting the resilient member 40. In that case, flatus exiting the stoma escapes along the interface between the membrane 42 and the stoma 28 to vent through a flatus vent (described later). Alternatively, the seal membrane 42 may of substantially liquid impervious, gas permeable material, in order to allow flatus to pass through the seal membrane 42 to a flatus vent. In either case, the seal membrane 42 may either be distinct and/or separate from the resilient member 40, it may be attached integrally to the resilient member 40, for example, by adhesive bonding or lamination.

Referring to FIG. 10, the seal membrane 42 may optionally form part of a chamber 44 enclosing the resilient member 40. The chamber 44 may be substantially fluid-tight, except for fluid flow controlled through one or more ports 46. The ports 46 may be configured to provide a fluid-damped dynamic response to an increase and/or decrease in degree of stoma protrusion. The fluid-damped response may temporarily increase the seal contact pressure to resist a temporary challenge from the stoma, for example, caused by flatus discharge or peristomal action. The ports 46 also allow pressure equalization over time to prevent excess pressure being applied for a prolonged period.

The resilient member 40 may be of polymeric foam. The foam may be open-cell foam, closed-cell foam, a memory foam, or a mix of both. Where used with an optional seal membrane 42, the membrane 42 may provide a smooth surface or skin for the cellular structure of the foam. The foam may have a Shore A hardness of less than 80, preferably less than 60, more preferably less than 50, or optionally less than 40 (especially if used with the seal membrane 42). Where no membrane 42 is used, the foam may optionally be of hydrophilic material, such that the foam absorbs moisture rapidly. The absorption results in expansion of the foam, causing the sealing effect to tighten against the stoma. Where a seal membrane 42 is used, hydrophilic material may be still be used if, for example, the membrane 42 (or at least a portion of the membrane surface) is liquid permeable to allow stomal fluid to reach the foam. Additionally or alternatively, resilient member 40 can be selected from a hydrophobic foam.

The stoma seal 22 (whether or not using a resilient member 40) may optionally be coated with an adhesive (48 in FIG. 9) to enhance the seal effect against the stoma 28. The adhesive can be applied to a portion of the seal surface or the entire seal surface. Adhesive may be selected from families comprising mucoadhesives and/or hydrocolloids which have been shown to be safe in providing the seal to mucosa membrane such as a stoma 28.

Figure 11:
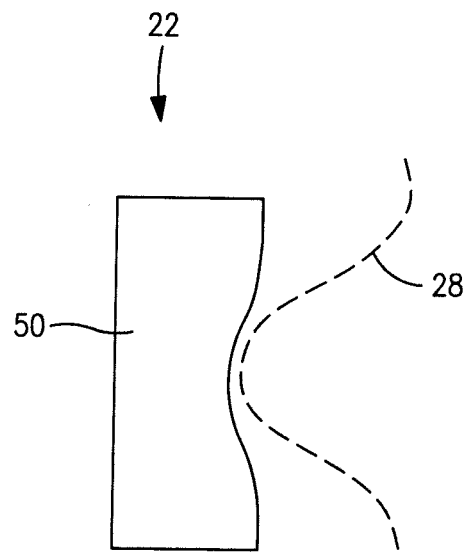
FIG. 11 is a schematic section showing in isolation a fourth example of stoma seal.

Referring to FIG. 11, a further example of stoma seal 22 comprises a gel or gel-forming material 50. The gel can be silicone gel, TPE gel, acrylic gel, hydrogel, hydrofiber (available from ConvaTec), etc. The gel provides a soft, compliant, skin-friendly seal in contact directly with the surface of the stoma 28. It is also envisaged that, in place of the adhesive 48 (FIG. 9), a gel or gel-forming material be applied as a surface coating to the seal 22.

Optionally, embodiments of the present invention are engineered to enhance control of the sealing pressure exerted between the seal 22 and the stoma 28. Especially in the case of an external, non-entrant seal 22, all of the sealing function is focused at the external surface of the stoma 28. At the external surface, effluent is already close to escaping from the stoma 28. This contrasts with an internal seal (e.g. a plug or bung) where the seal effect can be spread over a larger internal surface within the stoma. However, an external seal 22 used in the present embodiments is preferred as it can avoid complications and risks of an indwelling device. For an external seal 22 to be effective, the sealing pressure should be sufficient to counter the pressure of effluent at the stoma mouth. However, the seal should avoid prolonged application of excessive pressure, in order to avoid (i) any concerns over reduced blood flow in the stoma tissue, and/or (ii) any concerns regarding necrosis of stoma tissue.

In some embodiments, (e.g. as illustrated in FIGS. 5 and 7) a first technique positions the stoma seal 22 relative to the aperture 18 such that, when the appliance 10 is fitted in an operative wear position at the stoma 28, the stoma seal 22 does not touch, or does only slightly touch, the stoma 28. In such a quiescent state, there is no or only little seal pressure exerted between the stoma 28 and the stoma seal 22. For example, in this quiescent state, the sealing force may be no more than 1 psi, or preferably no more than 0.8 psi. Only when the stoma 28 is urged outwardly by natural causes, for example, as a result of peristomal action or of flatus or stool collecting near the stoma mouth, will the stoma 28 begin to bear more strongly against the stoma seal 22. The stoma seal 22 reacts by resists the outward movement of the stoma 28. Such an arrangement can generate a sealing pressure appropriate for resisting discharge of stomal effluent at the interface between the seal 22 and the stoma 28, according to the state of the stoma, while at the same time avoid sealing force being applied continuously all of the time while the appliance 10 is worn. At this extreme case of an urge of flatus or peristomal action, the sealing pressure may be no more than 2 psi (103.4 mm Hg). The ability to avoid continuous application of sealing pressure can reduce any impact that wearing a stoma seal may have on the stoma 28 itself. The appliance 10 can benefit from controlled discharge capability, but with the stoma-friendliness nearly matching that of a conventional ostomy pouch. If instead it is desired to maintain some degree of continuous sealing contact, e.g. for effluent that has a high proportion of liquid, the stoma seal 22 may be disposed closer to the aperture 18, for example, nearly flush with the surface of the first and second coupling members 20 and 24 (as indicated for example in FIG. 3).

Additionally or alternatively, in some embodiments, a second control technique is to configure the stoma seal 22 to be resilient yet soft and/or compliant. For example, the stoma seal is resiliently deformable, and is configured to generate a resilience reaction pressure of not more than about 2 psi, optionally not more than about 1 psi, further optionally not more than about 0.8 psi, when the stoma seal is compressed. Such a relatively soft stoma seal can provide excellent conformity to closely follow the contour of the stoma, while maintaining resilient contact with the contour. Such a soft characteristic is especially envisaged in combination with the use of foam for the resilient member 40.

In some embodiments, a third control technique uses the seal pressure exerted between the stoma seal 22 and the stoma 28 being supported or transferred, at least partly, by the second coupling member 24. Preferably, the second coupling member 24 bears at least a majority of the seal pressure, more preferably substantially all of the seal pressure (e.g. at least 90%). The second coupling member 24 may be configured to release or separate from a coupled condition with the counterpart member or surface 30 or 32 when the reaction pressure (or force) transmitted through the second coupling member 24 exceeds a seal threshold. The seal threshold of outer coupling member may be at least 10 N/in shear strength (i.e., 0 degree peel) or 5 psi such that the device will remain attached to the peristomal skin even though the inner coupling member is separated or released its contact against stoma. The use of such selective coupling strength for the inner and outer coupling member can ensure that the seal pressure applied to the stoma 28 by the stoma seal 22 does not exceed a safe level. In the event of the reaction to the seal pressure exceeding the seal threshold, the inner coupling member 24 will begin to separate or release, thereby to relieve the seal pressure. The seal threshold may be less than 50%, more preferably less than 20% of a corresponding threshold at which the outer coupling member 20 releases from the counterpart member or surface 30 or 32 to which the outer coupling member 20 couples in use. The second coupling member 24 may, for example, be sized or carry an adhesive configured to provide the desired coupling strength.

Various techniques are envisaged for mounting the seal 22 relative to the second coupling member 24. In the form illustrated in FIGS. 1, 5 and 6, the stoma seal 22 is accommodated by a seal holder 60. The stoma seal 22 projects from the holder through a second aperture 62 in the front wall 16 towards the first aperture 18 in the rear wall 14. The second aperture 62 is smaller in diameter than the first aperture 18. The second aperture 62 is sized to enable at least a stoma engaging part of the stoma seal 22 to project therethrough. The holder 60 comprises a mounting flange 64 from which depends a well or cup 66 for accommodating at least partly the seal 22. The mounting flange may be annular in shape, and sized to fit against the front wall 16 circumscribing the second aperture 62. The holder 60 may be substantially rigid, but it is preferred that the holder 60 have a self-supporting shape yet be deformable and/or flexible for the sake of comfort. The holder may, for example, be thermoformed.

In the present embodiment, the holder 60 also comprises one or more wells or recesses 68 for accommodating a deodorizing filter 70 and, optionally, a filter protection member 72. The filter protection member 72 serves to obstruct any semi-solid stool that may have leaked past the seal 22 from reaching the filter 70, while generally allowing flatus gas to pass relatively unhindered to the filter 70. For example, the filter protection member 72 may comprise open-cell foam, the pores of which tend to trap semi-solid stool while allowing flatus gas to pass through. The recess 68 may comprises one or more exit apertures communicating with the filter 70 for allowing deodorized gas to exit from the holder 60.

As best seen in FIG. 1, in some embodiments, the holder 60 comprises one or more radial castellations 74. The castellations 74 define radial channels through which flatus may pass between the surface of the holder 60 and the stoma seal 22, in order to reach the filter 70 and/or protection member 72. The castellations 74 also provide upstands for bearing against the stoma seal 22, in order to transmit the seal reaction pressure from the stoma seal 22, through the holder 60 and ultimately to the second coupling member 24.

Figure 6:
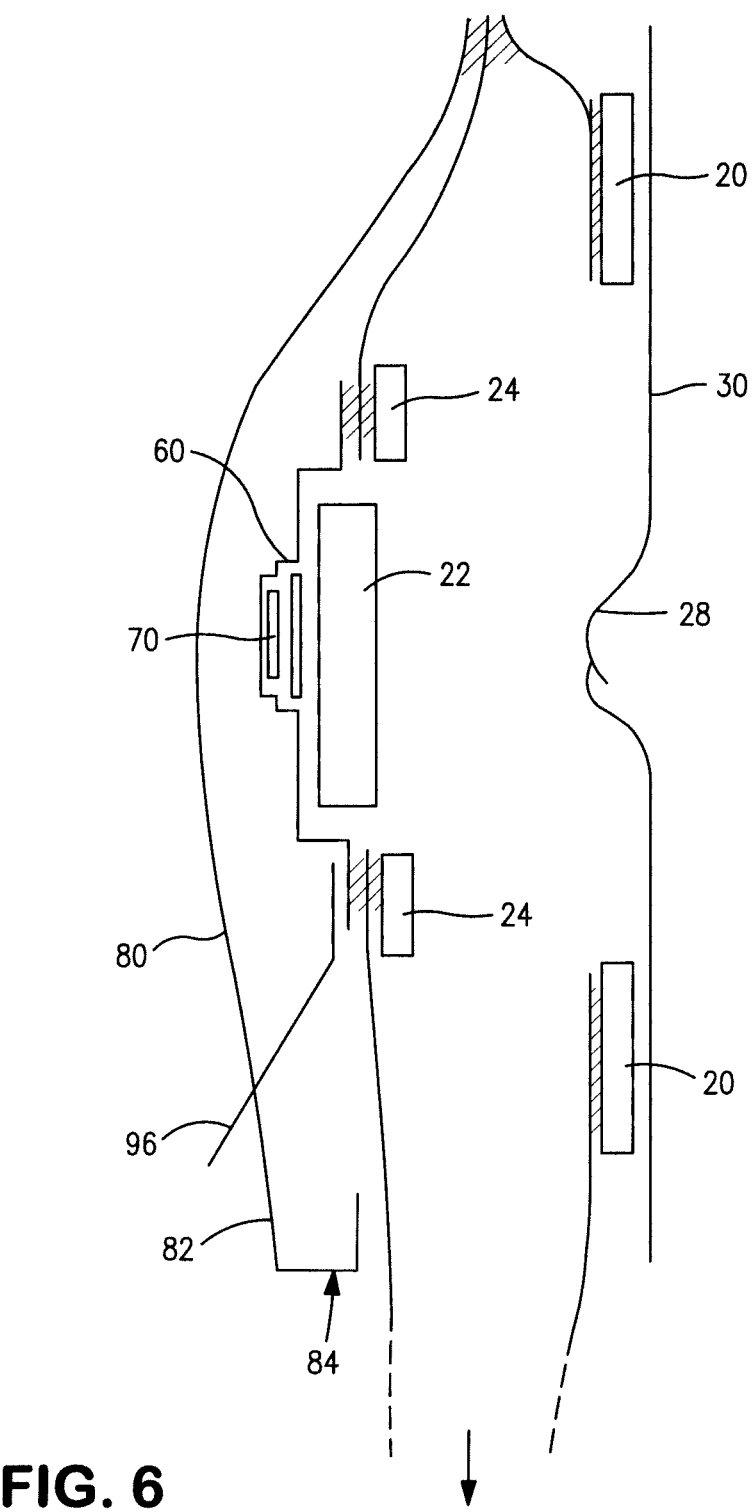
FIG. 6 is a schematic section similar to FIG. 5, but showing the seal displaced to permit stomal discharge.

As best seen in FIGS. 5 and 6, the holder 60 is attached, for example, by adhesive or welding, to the front wall 16 around the second aperture 62. The second coupling member 24 is likewise attached, by adhesive or welding, to the opposite face of the front wall 16 to provide a connection between the holder 60 and the second coupling member 24. The holder could, if desired, be attached directly to the second coupling member 24. However, the present construction may facilitate more straightforward manufacture. For example, the holder 60 may be attached to the front wall 16 after which the front wall 16 may be attached, by adhesive or welding, to the rear wall 14. Thereafter, the stoma seal 22 may be mounted to the holder 60 by inserting the stoma seal 22 through the first and second apertures 18 and 62, and the first and second coupling members 20 and 24 (which may be formed as an integral piece) may be attached substantially simultaneously to the respective surfaces of the rear and front walls 14 and 16.

In some embodiments, the appliance 10 further comprises a front fascia or cover 80. The cover 80 may be of comfortable flexible material, such as rubber or silicone. The cover 80 may be shaped to accommodate the projecting well or cup shape of the seal holder 60. Typically, the cover 80 comprises flatus vent apertures 76 through which the deodorized flatus, after exiting the holder, can vent externally of the appliance 10 (as indicated by the arrows in FIG. 5). In the illustrated embodiment, the cover 80 is dimensioned to cover substantially the entire upper portion 90 of the pouch 12.

Figure 4:
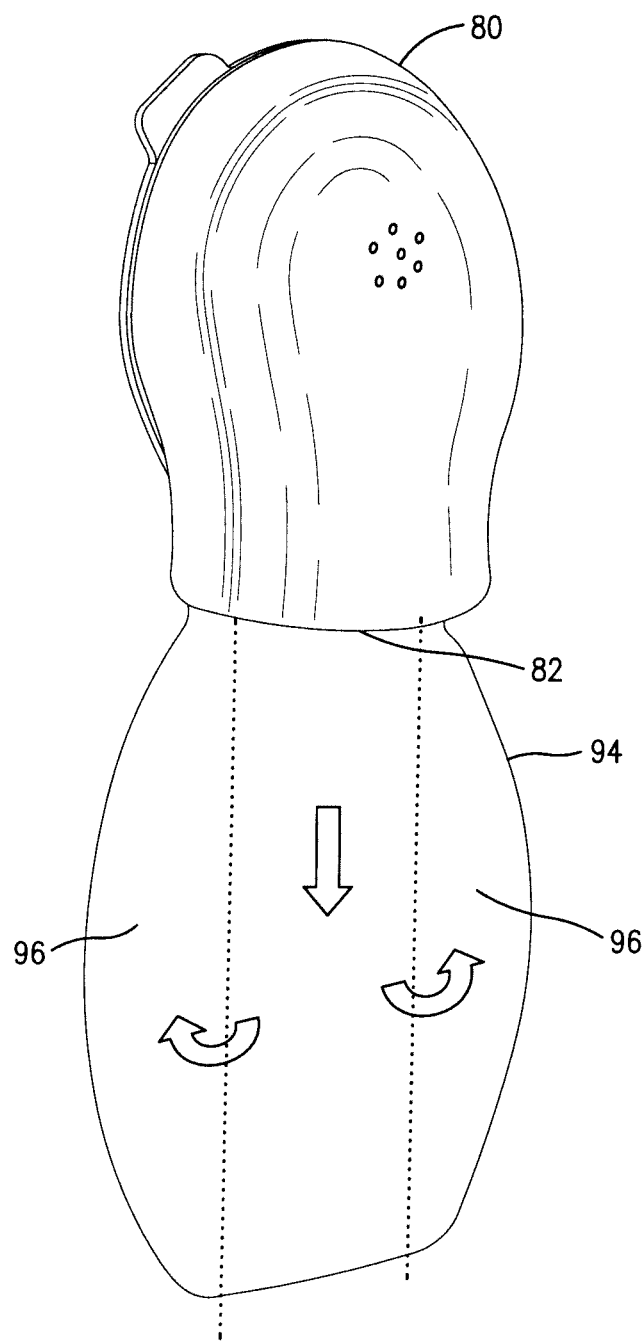
FIG. 4 is a schematic front perspective view of the first embodiment with the pouch deployed.

In some embodiments, the pouch 12 comprises the upper portion 90 (FIG. 1) and a lower portion 94 (FIG. 1) that is movable, relative to the upper portion 90, between a stowed and/or compact condition (FIGS. 2 and 5), and a distended and/or deployed condition (FIGS. 4 and 6). The upper portion 90 provides the apertures 18 and 62. In the compact condition, the lower portion 94 is folded or rolled upwardly towards the upper portion 90 to define a coil. The coil is held in its compact condition by any suitable means, such as by being received in a holding pocket 84 at the lower end 82 of the cover 80. Other retention means may include: hook and loop (or hook-hook) material; a magnetic fastener; interlocking or mating fastener elements (such as interlocking lips); pressure sensitive peelable adhesive. In its deployed condition, the lower portion 94 depends from the upper portion 90 to provide a collection volume for effluent.

Figure 2:
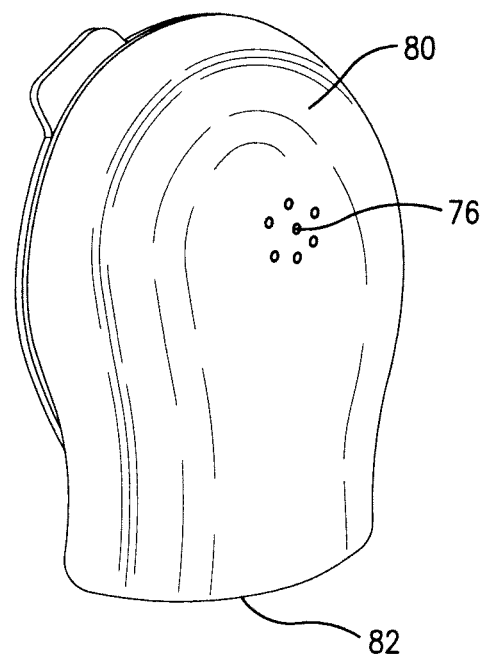
FIG. 2 is a schematic front perspective view of the first embodiment with the pouch in a stowed condition.

In some embodiments, a prosthetic ostomy appliance can be designed with a soft cover 80 and a compact device in a condition shown in FIGS. 2 and 5. Such a design is shown to be functional, discreet, and aesthetically appealing to ostomy users.

In some embodiments, the lower portion 94 is wider (in a plane of the pouch 12) than the upper portion 90 and/or a neck or waist 92 joining the upper and lower portions. In order to move the lower portion 94 to its stowed condition, at least one side region 96, and preferably both opposite side regions 96, is folded inwardly (e.g. about a broken line in FIG. 1), to reduce the width of the lower portion 94. The reduced width may be approximately the same as the width of the necked region 92. The reduced width lower portion 94 is then folded or rolled upwardly towards the upper portion 90. Referring to FIG. 4, deployment of the lower portion 94 involves the opposite order of unfolding. The lower portion 94 is distended downwardly, and the one or more folded-in side regions 96 unfold laterally (about the broken lines in FIG. 4) to define the fully distended shape. The large width of the lower portion 94 can provide a significant collection volume in a similar manner to a conventional ostomy pouch, yet fold to a smaller width compact form to be accommodated at the cover 80.

Referring especially to FIG. 5, the pouch 10 may be deployed either manually or automatically when the second coupling member 24 is disengaged to displace the stoma seal 22 and allow escape of stomal effluent into the pouch 10. In some embodiments, the action of manipulating the second coupling member 24 through the cover 80 bay releases the lower portion 94 to distend. In some embodiments, the weight of effluent collecting within the pouch 10 may be sufficient to release the lower portion 94 to distend. In some embodiments, the user may manually release the lower portion 94 to distend, such that the appliance permits the user to decide and control the desired configuration of the appliance.

Additionally or alternatively, a pulling tab 96 (FIGS. 5 and 6) is added to facilitate a manual separation of the inner coupling member 24. One end of such a pulling tab is connected to the front wall 16 or mounting flange 64. The other end is extended out of the soft cover 80 in order for an easy manipulation by ostomates in use. Optionally, the pulling tab extended outside of soft cover 80 can be attached to the front cover by an adhesive, mechanical seal, or a magnetic seal. For example, a peelable seal or a Velcro can be used to fasten the free moving end of pulling tab 96 to the soft cover 80.

Figure 12:
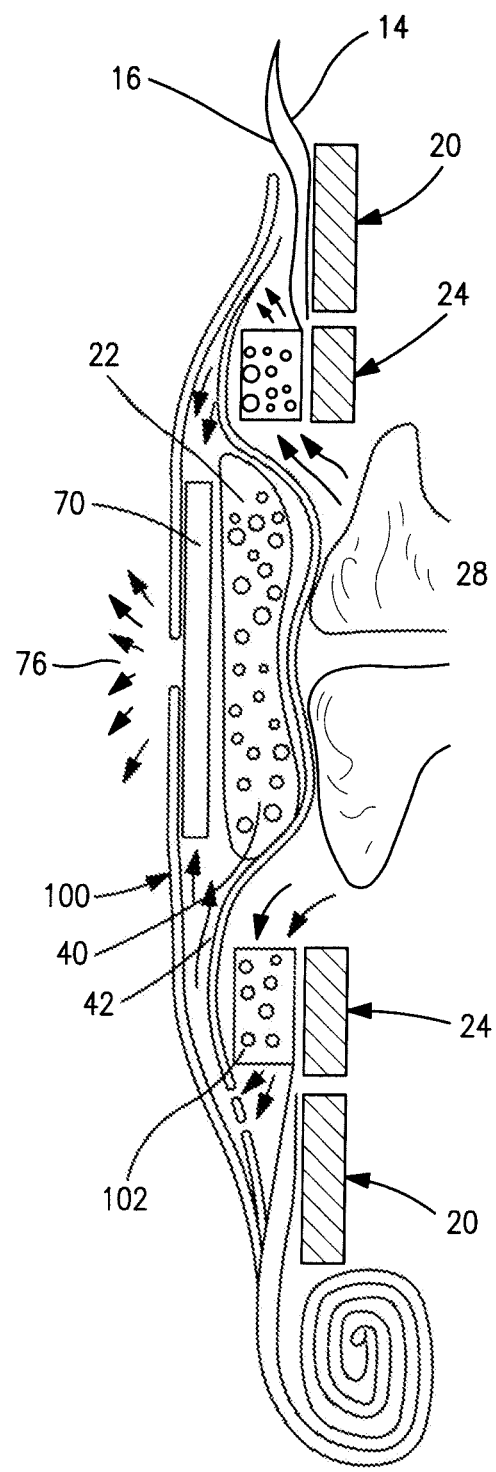
FIG. 12 is a schematic section showing a second embodiment of controlled discharge ostomy appliance.
Figure 13:
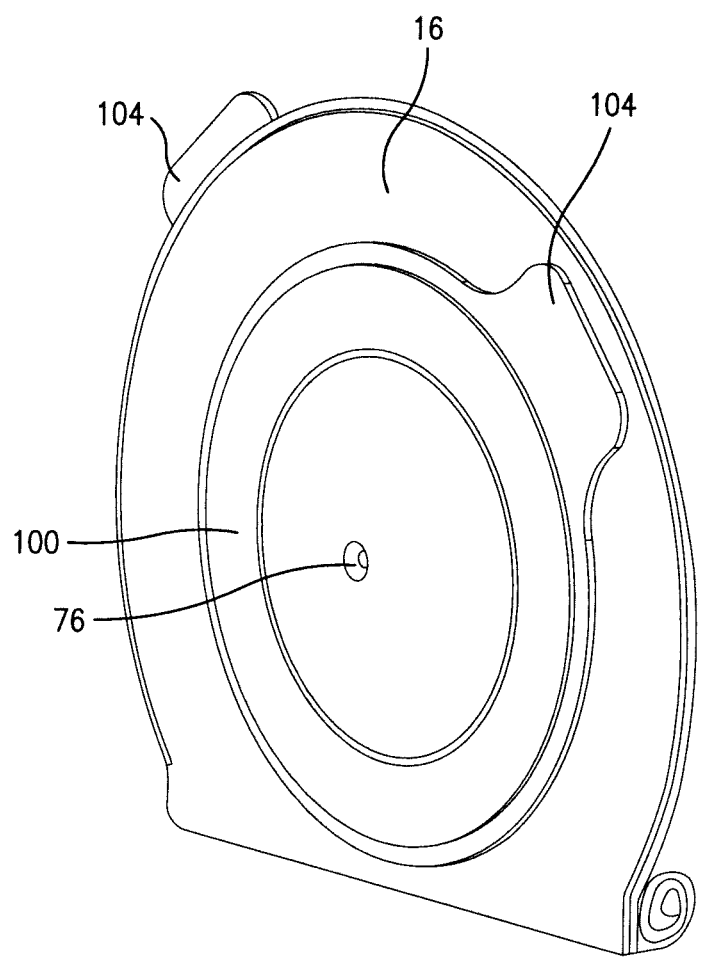
FIG. 13 is a schematic front perspective view of the second embodiment.

FIGS. 12 and 13 illustrate a second example of controlled discharge ostomy appliance, and the same reference numerals denote equivalent features. Whether or not shown, the second embodiment may include any combination of features from the first embodiment (for example, the side expanding lower portion of the pouch, not shown explicitly in FIGS. 12 and 13; and/or the body fitment not shown explicitly in FIGS. 12 and 13).

The main differences with the second embodiment are:

(i) The seal holder 60 and cover 80 of the first embodiment are replaced by a combined holder/cover 100, to which the seal membrane 42 is attached. The holder/cover 100 is attached to the second (front) wall 16 at a position outside the attachment of the second wall 16 to the second coupling member 24. A portion of the second wall 16 extending between the second coupling member 24 and the holder/cover 100 therefore acts as a form of pressure relieving suspension for the stoma seal 22. Should the pressure exerted by the stoma seal 22 on the stoma 28 exceed a threshold, the wall material of the second wall 16 will flex, allowing the stoma seal 22 to float partially with respect to the second coupling member 24, and thereby relieve excess seal pressure on the stoma.

An annular foam member 102 circumscribing the seal 22 acts as a phase separator allowing flatus to pass therethrough to the deodorizing filter 70, while obstructing passage of any solid or semi-liquid stool that might accidentally leak past the stoma seal 22. If desired, the foam member 102 may be omitted, and the seal membrane 42 comprise, at least over a part of its surface, a gas-permeable liquid-impermeable membrane material to allow flatus to pass directly through the membrane 42 to the deodorizing filter 70.

As best seen in FIG. 13, manipulation tabs 104 may be provided on, for example, the cover/holder 100 and the first (rear) pouch wall 14 to enable a user to apply a separation pressure to the second coupling member 24 through the appliance walls, without having to access the second coupling member 24 directly. Similar manipulation tabs may also be used with the first embodiment described herein.

The foregoing description is directed to preferred embodiments of the invention. Many modifications, improvements and equivalents may fall within the scope of any allowed claims.

The invention claimed is:

1. A controlled discharge ostomy appliance comprising:
a stomal aperture;
a non-entrant stoma seal;
an inner coupling member coupled to support the non-entrant stoma seal for retaining the non-entrant stoma seal in an operative position with respect to the stomal aperture, the operative position being selected such that, in use, a first seal pressure applied between the non-entrant stoma seal and a stoma when the stoma is quiescent is not more than about 1 psi, and a second seal pressure applied between the non-entrant stoma seal and the stoma when the stoma is active is greater than the first seal pressure and no more than about 2 psi;
an outer coupling member around the inner coupling member for supporting the controlled discharge ostomy appliance.

2. A controlled discharge ostomy appliance comprising:
a stomal aperture;
a non-entrant resilient stoma seal, the non-entrant resilient stoma seal being configured such that, when deflected from a non-compressed state, a resilient pressure generated by the non-entrant resilient stoma seal is not more than about 2 psi;
an inner coupling member coupled to support the non-entrant resilient stoma seal for retaining the stoma seal in an operative position with respect to the stomal aperture, the operative position being selected such that, in use, a first seal pressure applied between the non-entrant resilient stoma seal and a stoma when the stoma is quiescent is not more than about 1 psi, and a second seal pressure applied between the non-entrant resilient stoma seal and the stoma when the stoma is active is greater than the first seal pressure and no more than about 2 psi;
an outer coupling member around the inner coupling member for supporting the controlled discharge ostomy appliance.

3. The controlled discharge ostomy appliance of claim 2, wherein the resilient pressure generated by the non-entrant resilient stoma seal, when stoma seal is deflected, is selected from: not more than about 1 psi; not more than about 0.8 psi.

4. The controlled discharge ostomy appliance of claim 2, wherein the non-entrant resilient stoma seal comprises resilient compressible foam having a Shore A Hardness selected from: below about 60; below about 50; below about 40.

5. A controlled discharge ostomy appliance comprising:
a stomal aperture;
a non-entrant resilient stoma seal comprising resilient compressible foam having a Shore A Hardness selected from: below about 60; below about 50; below about 40;
an inner coupling member coupled to support the non-entrant resilient stoma seal for retaining the stoma seal in an operative position with respect to the stomal aperture, the operative position being selected such that, in use, a first seal pressure applied between the non-entrant resilient stoma seal and a stoma when the stoma is quiescent is not more than about 1 psi, and a second seal pressure applied between the non-entrant resilient stoma seal and the stoma when the stoma is active is greater than the first seal pressure and no more than about 2 psi;
an outer coupling member around the inner coupling member for supporting the controlled discharge ostomy appliance.

6. The controlled discharge ostomy appliance of claim 5, wherein the non-entrant resilient stoma seal further comprises a seal membrane covering a stoma engaging face of the resilient compressible foam.

7. A controlled discharge ostomy appliance comprising:
a stomal aperture;
a non-entrant resilient stoma seal;
an inner coupling member coupled to support the non-entrant resilient stoma seal for retaining the non-entrant resilient stoma seal in an operative position with respect to the stomal aperture, the operative position being selected such that, in use, a first seal pressure applied between the non-entrant resilient stoma seal and a stoma when the stoma is quiescent is not more than about 1 psi, and a second seal pressure applied between the non-entrant resilient stoma seal and a stoma when the stoma is active is greater than the first seal pressure and no more than about 2 psi, the inner coupling member being configured to separate from a counterpart surface when a pressure transferred through the inner coupling member exceeds a seal threshold, the seal threshold being not more than about 2 psi;
an outer coupling member around the inner coupling member for supporting the controlled discharge ostomy appliance, the outer coupling member being configured to form a stronger coupling to the counterpart surface than does the first coupling member.

8. The controlled discharge ostomy appliance of claim 7, wherein the outer and inner coupling members comprise adhesive.

9. A controlled discharge ostomy appliance comprising:
a first pouch wall having a first aperture;
a second pouch wall having a second aperture, the second aperture being smaller than and circumscribed by the first aperture;
a stoma seal holder attached to the second wall;
a stoma seal carried by the stoma seal holder, the stoma seal having a seal portion projecting through the second aperture towards the first aperture;
a first coupling member attached to the first wall and circumscribing the first aperture;
a second coupling member attached to the second wall, the second coupling member circumscribing the stoma seal, and the second coupling member being circumscribed by the first coupling member, the second coupling member retaining the stoma seal in an operative position with respect to the first aperture, the operative position being selected such that, in use, a first seal pressure applied between the stoma seal and a stoma when the stoma is quiescent is not more than about 1 psi, and a second seal pressure applied between the stoma seal and the stoma when the stoma is active is greater than the first seal pressure and no more than about 2 psi.

10. The controlled discharge ostomy appliance of claim 9, wherein the first and second coupling members are integral with each other.

11. The controlled discharge ostomy appliance of claim 10, wherein the first and second coupling members are joined by at least one frangible link.

12. The controlled discharge ostomy appliance of claim 9, wherein the first coupling member supports the stoma seal via the stoma seal holder for retaining the stoma seal in an operative position with respect to the first aperture.

13. The controlled discharge ostomy appliance of claim 9, further comprising a flexible cover mounted to at least one of the first and second pouch walls for covering the stoma seal holder.

14. A controlled discharge ostomy appliance comprising:
a stomal aperture;
a non-entrant stoma seal;
an inner coupling member coupled to support the non-entrant stoma seal for retaining the non-entrant stoma seal in an operative position with respect to the stomal aperture, the operative position being selected such that, in use, a first seal pressure applied between the non-entrant stoma seal and a stoma when the stoma is quiescent is not more than about 1 psi, and a second seal pressure applied between the non-entrant stoma seal and the stoma when the stoma is active is greater than the first seal pressure and no more than about 2 psi;
an outer coupling member around the inner coupling member for supporting the controlled discharge ostomy appliance;
a body fitment to which the inner and outer coupling members couple, the body fitment comprising skin adhesive adapted for adhering to the body and providing support for the inner and outer coupling members, the body fitment being captive to the appliance prior to engagement with the first and second coupling members.

15. The controlled discharge ostomy appliance of claim 14, wherein the body fitment is integrally coupled to at least one of the inner and outer coupling members by a flexible link.

16. The controlled discharge ostomy appliance of claim 14, wherein the skin adhesive comprises a moldable zone configured to be manually shaped to custom fit the stoma prior to engagement of the inner and outer coupling members against the body fitment.

17. The controlled discharge ostomy appliance of claim 14, wherein the outer coupling member is configured to form a non-separable coupling with the body fitment, and the inner coupling member is configured to form a separable coupling with the body fitment.

18. A controlled discharge ostomy appliance comprising:
a stomal aperture;
a non-entrant stoma seal;
an inner coupling member coupled to support the non-entrant stoma seal for retaining the non-entrant stoma seal in an operative position with respect to the stomal aperture, the operative position being selected such that, in use, a first seal pressure applied between the non-entrant stoma seal and a stoma when the stoma is quiescent is not more than about 1 psi, and a second seal pressure applied between the non-entrant stoma seal and the stoma when the stoma is active is greater than the first seal pressure and no more than about 2 psi;
an outer coupling member around the inner coupling member for supporting the controlled discharge ostomy appliance;
a body fitment to which the inner and outer coupling members couple, the body fitment comprising skin adhesive for adhering to the body and providing support for the inner and outer coupling members, the skin adhesive comprising a moldable zone configured to be manually shaped to custom fit the stoma prior to engagement of the inner and outer coupling members against the body fitment.

19. The controlled discharge ostomy appliance of claim 18, wherein the outer coupling member is configured to form a non-separable coupling with the body fitment, and the inner coupling member is configured to form a separable coupling with the body fitment.

20. A controlled discharge ostomy appliance comprising:
a stomal aperture;
a non-entrant stoma seal;
an inner coupling member coupled to support the non-entrant stoma seal for retaining the non-entrant stoma seal in an operative position with respect to the stomal aperture, the operative position being selected such that, in use, a first seal pressure applied between the non-entrant stoma seal and a stoma when the stoma is quiescent is not more than about 1 psi, and a second seal pressure applied between the non-entrant stoma seal and the stoma when the stoma is active is greater than the first seal pressure and no more than about 2 psi;
an outer coupling member around the inner coupling member for supporting the controlled discharge ostomy appliance;
a body fitment to which the inner and outer coupling members couple, the body fitment comprising skin adhesive for adhering to the body and providing support for the inner and outer coupling members,
wherein the outer coupling member is configured to form a non-separable coupling with the body fitment, and the inner coupling member is configured to form a separable coupling with the body fitment.

21. A controlled discharge ostomy appliance comprising:
a pouch having first and second walls;
a first aperture in the first wall for receiving a stoma;

a seal for selectively blocking discharge from the stoma into the pouch, the seal being in an operative position with respect to the first aperture, the operative position being selected such that, in use, a first seal pressure applied between the seal and the stoma when the stoma is quiescent is not more than about 1 psi, and a second seal pressure applied between the seal and the stoma when the stoma is active is greater than the first seal pressure and no more than about 2 psi;

wherein the pouch comprises an upper portion in which the first aperture is located, and a lower portion deployable from a folded-up condition to a distended condition, and in the folded-up condition, at least one side region of the lower portion is folded inwardly to define a lower portion of reduced width.

22. The controlled discharge ostomy appliance of claim 21, wherein the at least one side region is unfoldable upon deployment of the lower portion it is deployed condition, to achieve a full width of the lower portion.

23. The controlled discharge ostomy appliance of claim 21, wherein the lower portion in its deployed condition is wider in a plane of the pouch than at least one selected from: the upper portion of the pouch; a necked portion between the upper and lower portions.

24. A controlled discharge ostomy appliance comprising:
a pouch having first and second walls;
a first aperture in the first wall adapted for receiving a stoma;
a seal for selectively blocking discharge from the stoma into the pouch, the seal being in an operative position with respect to the first aperture, the operative position being selected such that, in use, a first seal pressure applied between the seal and the stoma when the stoma is quiescent is not more than about 1 psi, and a second seal pressure applied between the seal and the stoma when the stoma is active is greater than the first seal pressure and no more than about 2 psi;
wherein the pouch comprises an upper portion in which the first aperture is located, and a lower portion deployable from a folded-up condition to a distended condition, and the controlled discharge ostomy appliance further comprises: a flexible cover that substantially covers the second wall in the upper region of the pouch, the flexible cover comprising a retainer for retaining the lower portion of the pouch in the folded-up condition.

25. A controlled discharge ostomy appliance comprising:
a pouch having first and second walls, the first wall including a stomal aperture;
a non-entrant stoma seal;
an inner coupling member coupled to support the non-entrant stoma seal for retaining the non-entrant stoma seal in an operative position with respect to the stomal aperture, the operative position being selected such that, in use, a first seal pressure applied between the non-entrant stoma seal and a stoma when the stoma is quiescent is not more than about 1 psi, and a second seal pressure applied between the non-entrant stoma seal and the stoma when the stoma is active is greater than the first seal pressure and no more than about 2 psi;
an outer coupling member around the inner coupling member for supporting the controlled discharge ostomy appliance;
a cover of flexible impact-absorbing material covering at least a portion of the second wall opposite the stomal aperture.

26. The controlled discharge ostomy appliance of claim 25, wherein the pouch comprises an upper portion in which the first aperture is located, and a lower portion deployable from a folded-up condition to a distended condition, and wherein the cover covers the second wall in the upper region of the pouch.

27. A prosthetic controlled discharge ostomy appliance comprising:
a stomal aperture;
a non-entrant stoma seal;
an inner coupling member coupled to support the non-entrant stoma seal for retaining the non-entrant stoma seal in an operative position with respect to the stomal aperture, the operative position being selected such that, in use, a first seal pressure applied between the non-entrant stoma seal and a stoma when the stoma is quiescent is not more than about 1 psi, and a second seal pressure applied between the non-entrant stoma seal and the stoma when the stoma is active is greater than the first seal pressure and no more than about 2 psi;
a pouch having first and second walls, the first wall including the stomal aperture;
an outer coupling member around the inner coupling member for supporting the prosthetic controlled discharge ostomy appliance;
a cover of flexible impact-absorbing material covering at least a portion of the second wall opposite the stomal aperture.

28. The prosthetic controlled discharge ostomy appliance of claim 27, wherein the cover of flexible impact absorbing material comprises a rubber or thermoplastic elastomer having a Shore A Hardness selected from: below about 80, below about 60, below about 40.

29. The prosthetic controlled discharge ostomy appliance of claim 27, further comprises a pulling tab to facilitate the manual separation of the inner coupling member.

30. The prosthetic controlled discharge ostomy appliance of claim 27, wherein the non-entrant stoma seal is provided for selectively blocking discharge from the stoma into the pouch.

31. The prosthetic controlled discharge ostomy appliance of claim 30, wherein the pouch comprises an upper portion in which the stomal aperture is located, and a lower portion deployable from a folded-up condition to a distended condition, and in the folded-up condition, at least one side region of the lower portion is folded inwardly to define a lower portion of reduced width.

32. The prosthetic controlled discharge ostomy appliance of claim 31, further comprises a pulling tab to facilitate the manual deployment of the pouch from the folded-up condition to the distended condition.

* * * * *